United States Patent [19]
Ross

[11] Patent Number: 5,307,679
[45] Date of Patent: May 3, 1994

[54] METHOD AND APPARATUS FOR EVALUATING THE DRYING PROPERTIES OF UN-DRIED WOOD

[75] Inventor: Robert J. Ross, Madison, Wis.

[73] Assignee: The United States of America as represented by the Secretary of Agriculture, Washington, D.C.

[21] Appl. No.: 857,146

[22] Filed: Mar. 25, 1992

[51] Int. Cl.[5] .................. G01H 5/00; G01N 29/18; G01N 29/20; G01N 29/00
[52] U.S. Cl. .................................................. 73/597
[58] Field of Search ............... 73/73, 597, 24.04, 598

[56] References Cited

U.S. PATENT DOCUMENTS

| | | |
|---|---|---|
| 3,074,267 | 1/1963 | Martin . |
| 3,190,111 | 6/1965 | Trussell et al. . |
| 3,327,523 | 6/1967 | Kelemencky et al. ............... 73/639 |
| 3,354,699 | 11/1967 | Carnevale et al. ................... 73/598 |
| 3,384,767 | 5/1968 | Arnold et al. ....................... 73/600 |
| 3,513,690 | 5/1970 | Pellerin et al. . |
| 3,531,983 | 10/1970 | Heath et al. ......................... 73/579 |
| 3,600,937 | 8/1971 | Nilberg ................................. 73/598 |
| 3,664,180 | 5/1972 | McDonald et al. .................. 73/598 |
| 3,877,294 | 4/1975 | Shaw .................................... 73/579 |
| 3,991,603 | 11/1976 | Wonn et al. ...................... 73/24.04 |
| 4,160,387 | 7/1979 | Ihara et al. ........................... 73/639 |
| 4,566,084 | 1/1986 | Laine .................................... 73/597 |
| 4,750,368 | 6/1988 | Shearer et al. ....................... 73/618 |
| 4,838,085 | 6/1989 | Pellerin et al. ...................... 73/597 |
| 4,876,889 | 10/1989 | Shakkottai et al. .................. 73/597 |
| 4,941,356 | 7/1990 | Pallaske ............................... 73/587 |
| 4,941,357 | 7/1990 | Schajer ................................ 73/600 |
| 5,237,870 | 8/1993 | Fry et al. .............................. 73/598 |

FOREIGN PATENT DOCUMENTS

| | | | |
|---|---|---|---|
| 0002650 | 1/1983 | Japan ................................... 73/598 |
| 0167263 | 7/1988 | Japan ..................................... 73/73 |
| 1499130 | 8/1989 | U.S.S.R. ............................... 73/597 |
| 9108477 | 6/1991 | World Int. Prop. O. .............. 73/73 |

OTHER PUBLICATIONS

Stress Wave Speed and MOE of Sweetgum Ranging from 150 to 15 percent MC, Forest Products Journal, dated Oct. 1974.
NDE of Green Material With Stress Waves: preliminary results using dimension lumber, Forest Products Journal, dated Aug. 1989.
Identifying Bacterially Infected Oak by Stress Wave Nondestructive Evaluation USDA Forest Service Research Paper FPL-RP-512, dated Mar. 1992.

*Primary Examiner*—Diego F. F. Gutierrez
*Attorney, Agent, or Firm*—M. Howard Silverstein; John D. Fado; Janet I. Stockhausen

[57] ABSTRACT

A method of evaluating un-dried lumber for its propensity to degrade, during drying couples an acoustic pulse to un-dried lumber and measures the speed of the propagating of the pulse through the lumber. Preferably, the pulse is directed transversely to the lumber's grain. The pulses may be generated by a calibrated weight striking the lumber's surface and detected at two points on the lumber by means of acoustically coupled accelerometers. A timer, triggering on similar portions of the acoustic pulse as detected at the two points provides the necessary information to deduce speed. A speed threshold is determined empirically by studying samples of the lumber type and the speed of acoustic pulses through them and drying them to determine their propensity to degrade.

10 Claims, 2 Drawing Sheets

METHOD AND APPARATUS FOR EVALUATING THE DRYING PROPERTIES OF UN-DRIED WOOD

BACKGROUND OF THE INVENTION

1. Field of the Invention

This invention relates generally to the testing of wood and specifically to testing un-dried or partially dried wood to evaluate its propensity to degrade upon drying, for example, by splitting.

2. Background Art

At a microscopic level, wood is composed of a collection of slender, tubular fibers aligned longitudinally along the axis of the trunk of the tree. The substantially longitudinal alignment of these fibers defines the grain of the wood.

Freshly felled lumber (henceforth termed "un-dried wood) contains considerable moisture. The total amount of stored water, or the "moisture content" of wood is typically expressed as a percentage of the weight of the stored water to the weight of the dry wood. The moisture content of un-dried wood, for example, may exceed 100%, indicating a weight of stored water greater than that of the dried wood. Alternatively, the amount of moisture stored in the wood may be expressed with respect to a "fiber saturation point" being defined as a point during the drying of wood, where the free water has first disappeared from the lumens of the fibers. Un-dried wood typically has a moisture content above the fiber saturation level.

The stored moisture in un-dried wood creates three problems: 1) it increases the weight of the wood, and 2) it increases the wood's susceptibility to decay, and 3) it creates the problem of spontaneous shrinkage of the wood when the wood is exposed to ambient, low humidity conditions in an assembled structure.

For this reason wood is typically dried, either by exposing the wood to the open air in loosely stacked racks, "air drying", or by drying the wood in the controlled atmosphere of a kiln, "kiln drying". Kiln drying represents a considerable improvement in drying speed over air drying, the latter which may require a month of drying time for boards up to an inch thick and more than a year for certain hardwoods or for thicker lumber. In contrast, kiln drying of most boards may be accomplished within a few weeks.

This improvement in drying time, in kiln drying, substantially decreases the lumber's final cost. Nevertheless, kiln drying is not costless and it is important to use the kiln efficiently. Efficient use of the kiln requires the careful selection of the kiln drying speed: if the drying speed is too slow, the total cost of the drying procedure will be unnecessarily increased, if the drying speed is too fast, however, undue checking and warpage of the wood will occur.

As the wood is dried it shrinks, but not equally along and across its grain. The alignment of wood's fibers makes wood an anisotropic material, that is, one which has varying physical properties along its different axes. Specifically, wood shrinks a proportionally greater amount in the transverse direction, perpendicular to the grain, also its direction of least tensile strength. This combination of factors creates the potential for checks as the wood is dried, that is, cracks or splits along the grain. Extensive checking along greater than two axes is termed honeycombing.

Splitting, honeycombing, and checking of dried wood all degrade the lumber, both aesthetically, and by reducing the strength of the wood. Even so, typically, a certain percentage of the lumber in a properly operated kiln will exihibit drying induced degradation. This is because of variation in the propensity of different pieces of lumber, even of the same wood type, to degrade upon drying, and because of an inability to determine this propensity to degrade when the wood is in the un-dried state.

The same problems apply to partially dried lumber, that is, lumber that has had some drying but not so much that the degradation is apparent. Thus the term "un-dried", should be understood to include not only fresh cut lumber but lumber that has not dried to the point where degradation occurs.

Of particular concern with regard to drying induced degradation is a condition called "wetwood". Wetwood is an abnormally high concentration of water in un-dried lumber thought to be caused by the operation of bio-deteriorants, e.g. anaerobic bacteria. Although it may be identified by a translucent or water soaked appearance, and a sour or rancid odor, generally, wetwood cannot be detected until during or after the drying process when it results in checking or splitting or honeycombing of the dried lumber. Importantly, un-dried wetwood may not exhibit significant differences in strength from normal wood not prone to degrading.

Wetwood and other such conditions that render a piece of wood "hard to dry" increase the expense of kiln dried lumber, both through the lost value of the degraded lumber and through the cost of the kiln space wasted in drying this lumber. To a lesser extent, the incidence of hard to dry lumber may also increase the cost of kiln drying by encouraging slower than necessary drying times for the remainder of the lumber.

SUMMARY OF THE INVENTION

The present invention provides a method of assessing the propensity of un-dried or partially dried wood to degrade, thus allowing un-dried wood to be sorted and dried according to this quality.

Specifically, an acoustic pulse is induced in the un-dried wood and the speed of transmission of that pulse is measured. This pulse speed is compared to a reference speed to determine whether the lumber will be hard to dry.

It is thus one object of the invention to provide means for evaluating whether a given board will be hard to dry prior to the drying operation. It has been determined that the transmission speed of the acoustic pulse through un-dried wood is related to the propensity of the wood to split during drying.

It is another object of the invention to develop a non-destructive test for determining whether a piece of wood is hard to dry. The use of an acoustic pulse to evaluate the wood avoids damage to the wood, such as might be caused by techniques that require cutting samples from boards for test drying, for example. In theory, the present invention could evaluate the entire volume of each board prior to drying.

It is yet another object of the invention to provide a test for un-dried wood's propensity to degrade upon drying that is simple and suitable for use in the lumber industry. The instrumentation needed for the measurement and generation of acoustic waves is readily available and other similar acoustic measuring systems have been proven in the environment of lumber processing.

Other objects and advantages besides those discussed above shall be apparent to those experienced in the art from the description of a preferred embodiment of the invention which follows. In the description, reference is made to the accompanying drawings, which form a part hereof, and which illustrate one example of the invention. Such example, however, is not exhaustive of the various alternative forms of the invention, and therefore reference is made to the claims which follow the description for determining the scope of the invention.

DETAILED DESCRIPTION OF THE PREFERRED EMBODIMENT

Figure 1:
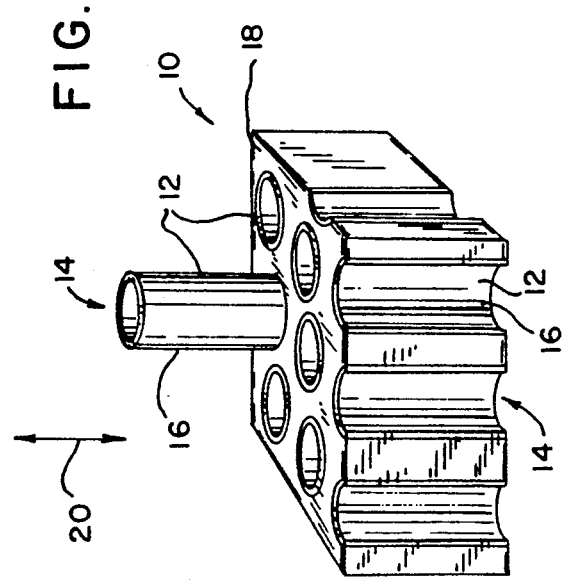
FIG. 1 is a schematic representation of a small volume of wood, greatly enlarged, and showing the elongate tubular fibers which define the grain of the wood.

Referring to FIG. 1, a highly simplified depiction of a volume of un-dried wood 10 includes of a bundle of elongate, tubular, fibers 12 having lumens 14 whose axes are aligned longitudinally along a grain axis 20 parallel to the axis of the trunk of the tree from which the un-dried wood 10 was obtained. A cell wall 16 surrounds and defines the lumen 14 and is bound to the cell walls 16 of the other fibers 12 by an intercellular material 18.

The moisture of the un-dried wood 10 is held in part as free water (not shown) in the lumens 14 with the remainder distributed through the cell wall 16 and the intercellular material 18. During the drying of the un-dried wood 10, moisture moves from the lumens 14, the cell walls 16, and the intercellular material 18 resulting in a shrinkage of the fibers 12 and hence the un-dried wood 10. As described above, this shrinkage may degrade the dried wood.

Figure 2:
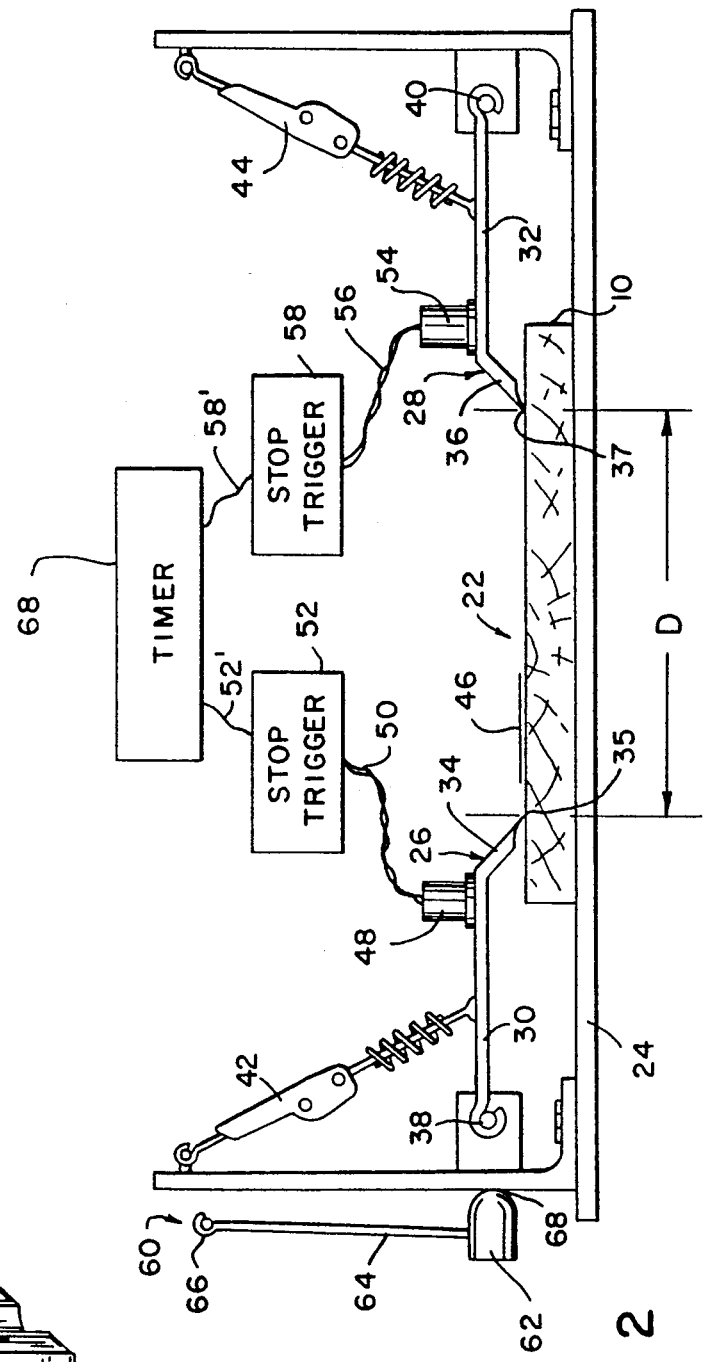
FIG. 2 is an elevational view of a first embodiment of an apparatus according to the present invention showing the positioning of transducers on either side of a board to be tested with associated timing circuitry shown in block diagram form.

Referring to FIG. 2, in a first embodiment of the present invention, un-dried wood 10 in the form of a plank 22 is placed with its broad face horizontally supported by a planer table 24. Table 24 is generally smooth to permit the sliding of the plank 22 along its surface, to facilitate measurements at multiple points along the plank's length, and is preferably composed of a hard, dense material having acoustic property substantially different from that of the plank 22 to reduce, to the extent possible, the coupling of acoustic energy from the plank 22 into the table 24.

Plank 22, as shown, is a finished board, however it should be understood that the present invention is also suitable for use on rough timber or unprocessed logs and hence can be used to make primary processing decisions, e.g., decisions as to whether to harvest or process a particular tree, and is suitable for use in the field. In the latter case the table 24 is not required but may be supplanted by a clamp or other supporting structure (not shown).

The plank 22 is held downward against the table 24 by means of opposed clamp fingers 26 and 28 each having a generally horizontal beam portion 30 and 32 respectively connected to downwardly sloping tips 34 and 36. Tips 34 and 36 contact the upper surface of the plank 22, as it rests on the planer table 24, at contact points 35 and 37; its left and right edges respectively separated by a predetermined distance D.

Attached to the other end of the beam portions 30 and 32, removed from the tips 34 and 36 of the respective clamp fingers 26 and 28, are pivots 38 and 40 which allow slight downward motion of the beam portions 30 and 32 and the tips 34 and 36 to insure the tips 34 and 36 make contact at points 35 and 37 on the upper surface of the plank 22 regardless of slight dimensional variations in the plank 22.

Spring loaded clamps 42 and 44, attached to the beam portions 30 and 32, open to allow raising of the clamp fingers 26 and 28 away from the plank 22, and close to provide a compressive force downward against the beam portions 30 and 32, pivoting the clamp fingers 26 and 28 about pivots 38 and 40 to hold the tips 34 and 36 firmly against the upper surface of the plank 22. The compressive force provided by the clamps 42 and 44, when in the closed position, is such as to ensure good acoustic coupling between the clamp fingers 26 and 28 and the plank 22.

An axis 46, defined as the line between the point of contact 35 and 37 of tips 34 and 36 with the plank 22, is arranged to run generally transverse to the grain 20 (not shown) of plank 22.

Attached to the horizontal beam portion 30 of the first clamp finger 26 is an accelerometer 48 having an axis of sensitivity generally aligned with axis 46. The accelerometer 48 is connected by flexible leads 50 to start trigger circuitry 52 to be described.

Similarly, a second accelerometer 54, having its axis of sensitivity also parallel to axis 46 and oriented to give the same polarity measurement of acceleration as accelerometer 48, is attached to the horizontal beam portion 32 of clamp finger 28. Flexible leads 56 connect accelerometer 54 to stop trigger circuitry 58 also to be described below.

It will be understood from this description that accelerometer 48 and 54, coupled to plank 22 via the compression of the clamp fingers 26 and 28 against the upper surface of the plank 22, may measure the acceleration of plank 22. The material of the clamp fingers 26 and 28 is constructed of an extremely rigid material, such as steel, so as to accurately communicate the actual accelerations of the plank 22 at the points 35 and 37 to the spatially removed accelerometers 48 and 54 and thus to approximate the result of the mounting of accelerometers 48 and 54 directly on the plank 22, which is avoided in practice to allow easy repositioning of the plank 22.

A hammer 60 having a weighted head 62 attached to a swing arm 64 hangs freely from a pivot 66 positioned above the plank 22 so that the hammer 60 may swing through an arc, downward to the left edge of the plank 22 and strike the end of the beam part 30, removed from tip 34, horizontally at a point 68. The beam 30 serves to couple this acoustic pulse into the plank 22 though tip 34. The energy and momentum of the hammer 60 may be predetermined by adjusting the weight of the hammer head 62 and the height to which it is raised in its swing prior to its release above the impact point 68. The shape of the head of the hammer is not critical and it may be pointed, blunt or inbetween. The results attained are likely to be more accurate if the contact area between the hammer head and the wood to be tested is narrowly defined but reasonable, usable results are attainable using a variety of shapes for the hammer head.

It is important only that the impact point 68 is adjusted to lie generally along axis 46 on the far side of point 35 with respect to point 37. This permits the striking of the hammer head 62 against the beam 30 at point 68 to produce an acoustic wave progressing first past point 35, to be measured by accelerometer 48, and then past point 37, to be measured by accelerometer 54.

It will be recognized that the acoustic wave created by the impact of the hammer 60 against the beam 30 travels a short distance through tip 34 after it has passed accelerometer 48 but before it reaches plank 22. Likewise, the acoustic pulse leaves plank 22 and travels for a short distance through tip 36 prior to reaching accelerometer 54. The effect of these distances along tips 34 and 36, between points 35 and 37 and their respective accelerometers 48 and 54, on the calculation of sound speed through the plank 22 may be easily compensated for because their effect on the measured speed of the acoustic pulse is essentially constant. Further, these distances are as a practical matter kept small so their effect is minimized.

Figure 3:
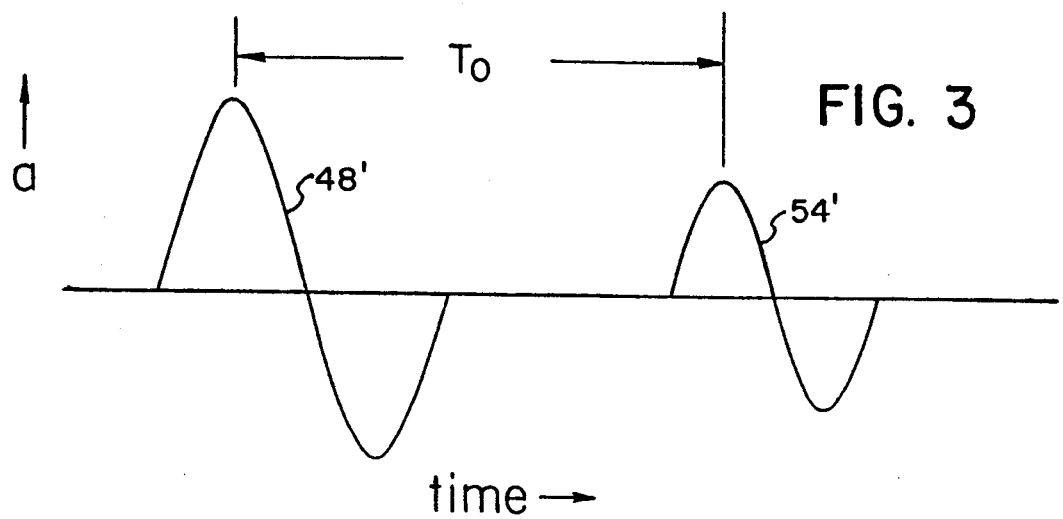
FIG. 3 is a simplified diagram of the combined waveform of the transducers shown in FIG. 2 plotted against time and showing the point of trigger of the timing circuitry employed to determine the speed of the pulse traveled through the board to be tested.

Referring to FIG. 3, the signal 48' from accelerometer 48 and the signal 54' from the accelerometer 54, caused by the acoustic wave from the impact of hammer 60 against the beam 30, approximate a single sinusoidal cycle, the positive-going lobe of the cycle reflecting a positive acceleration caused by the advancing shock wave through plank 22 from the impact of hammer 60 and the negative-going lobe of the cycle reflecting a negative acceleration of the elastic return of the wood 10 of the plank 22.

Signal 54' precedes signal 48' as a result of the proximity of point 35, associated with accelerometer 48, to the impact point 68 of the hammer 60. Signal 54' is also of lesser amplitude than signal pair 48' as a result of the natural damping affect of the wood 10, that is, the intrinsic property of the wood to absorb and dissipate acoustic energy.

Signals 48' and 54' are received by the start trigger 52 and stop trigger 5 respectively to produce trigger signals 52' and 58' respectively. The start trigger 52 and the stop trigger 58 may be either simple threshold detectors, comparing the voltages of signals 48' or 54' to a threshold voltage and providing trigger signals 52' or 58' when the threshold voltage is exceeded by signals 48' or 54'; or peak detectors providing trigger signals 52' or 58' when the peak of signals 48' or 54' is detected. Both such trigger circuits are well known in the art. Importantly, the start trigger 52 and stop trigger 58 are set to trigger on the same relative portions of signal 48' and signal 54' to establish a time $t_0$ indicating the time it takes the acoustic wave caused by impact of hammer 60 to pass from point 35 to point 37, thus traversing distance D.

Trigger signal 52' is connected to a "start" input of timer 68 to start the timing function and trigger signal 58' is connected to a "stop" input of timer 68 to stop the timing function and to indicate thereby the duration between the signals 48' and 54' and thus to provide an accurate measurement of time $t_0$. Timer 68, start trigger 52 and stop trigger 58 are commercially available as a single unit from a variety of manufacturers of test equipment including Metriguard of Pullman, Wash. For typical application with commercially sized lumber, timer 68 must have a resolution of less than 1 microsecond.

It will be understood from the foregoing description, that after the impact of the hammer 60 against the beam 30, the value indicated on the timer 68 will be essentially the time required for the acoustic wave to travel the distance D through the plank 22.

From D, the sound speed $c_0$ in the plank 22 transverse to the grain 20 may be readily determined by dividing D by $t_0$. The evaluation of the plank 22 is made by comparing the sound speed $c_0$ to a empirically derived speed threshold $c_1$ for that type of material. The empirically derived speed threshold $c_1$ is produced by examining a number of samples of the wood type in question and then drying them to determine their propensity to degrade upon drying.

A speed $c_0$ greater than this threshold $c_1$ indicates wood that is relatively easy to dry whereas a speed $c_0$ below this threshold $c_1$ indicates wood that is relatively hard to dry—frequently wetwood. The threshold $c_1$ is conveniently centered in a range accommodating a small amount of uncertainty in the process, or several thresholds $c_1$-$c_n$ may be established to distinguish between degrees of susceptibility to drying induced degradation.

It will be understood that for practical purposes, if the distance D is held constant, a time threshold $t_1$ may be substituted for the speed threshold $c_1$ so that the evaluation of the plank 22 may be made directly from the time indicated by timer 68.

EXAMPLE

The above described apparatus was used to evaluate 2,477 board feet of 4/4 oak lumber. Among the tested lumber were 371 red oak boards comprising 1,809 board feet, 45% of which had bacterially infected heartwood creating a wetwood condition. Also included were 136 white oak boards comprising 668 board feet, 34% of which had bacterially infected heartwood creating a wet wood condition. The boards were distributed among five lumber grades:

FAS and Selects (783 board feet),
No. 1 Common (748 board feet),
No. 2 Common (521 board feet), and
No. 3a Common (425 board feet).

A time thresholds $t_0$ of 250 ms was established for the red and white oak respectively equating to speeds of 4,000 feet per second. The following tabulation shows the percentage of boards that were correctly identified as having over 70% bacterial heartwood creating a wetwood condition:

| Boards | Species | Grade Bacterial |
|---|---|---|
| | Red Oak | |
| FAS/Selects | 89% | |
| Common | 92% | No. 1 |
| Common | 97% | No. 2 |
| Common | 97% | No. 3a |
| | White Oak | |
| FAS/Selects | 14% | |
| Common | 56% | No. 1 |
| Common | 71% | No. 2 |
| Common | 73% | No. 3a |

These results indicate that the sound speed tests are extremely likely to detect the presence of bacterial heartwood forming wetwood in red oak lumber, and likely to detect the condition in all but select white oak. All the boards tested were un-dried lumber.

Figure 4:
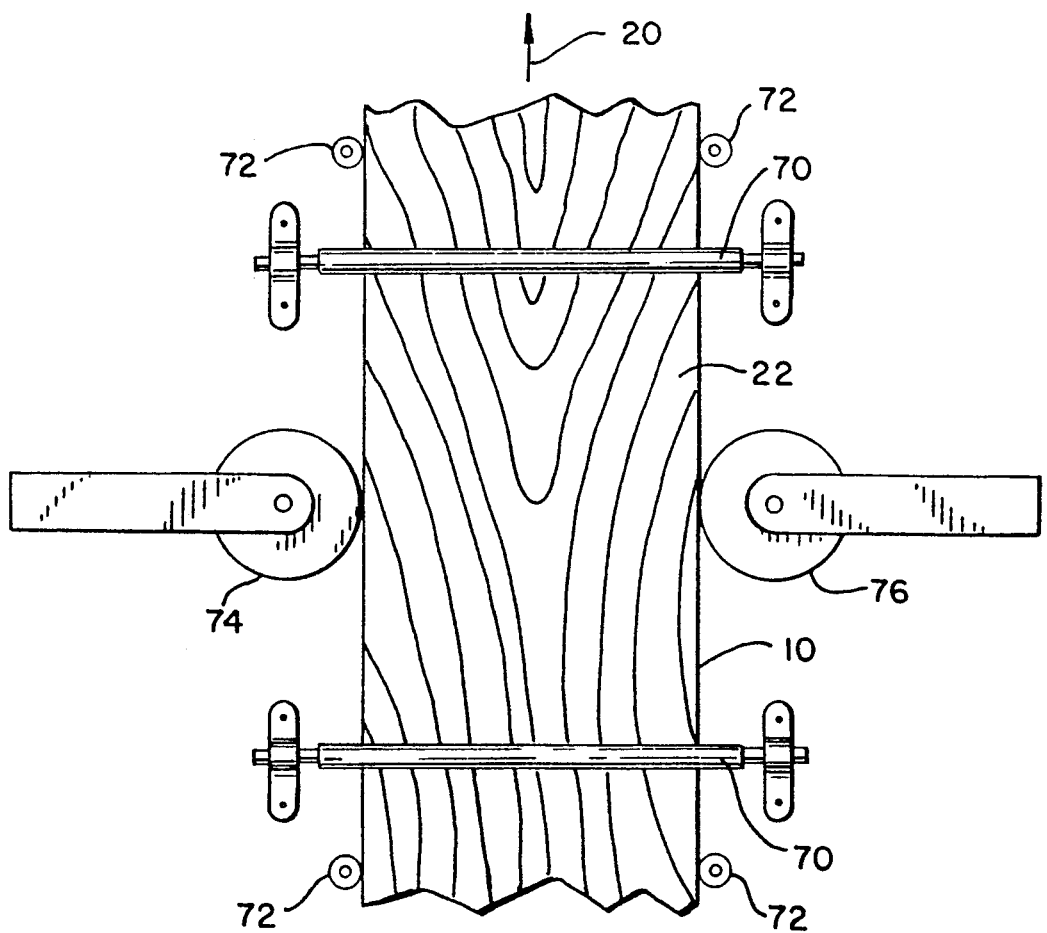
FIG. 4 is a plan view of a second embodiment of the invention intended for continuous measuring of lumber in an industrial environment and employing roller-type transducers.

FIG. 4, in a second embodiment adapted to a commercial production environment, the plank 22 is moved continuously along the direction of its grain 20 as guided by a series of rollers 70 along its broad faces and rollers 72 along its left and right edges. The accelerometers 48 and 54 and hammer 60 of the embodiment of FIG. 2 are replaced with opposed piezoelectric transducers 74 and 76, constructed as disks and provided with axles to roll along the left and right edges of the plank 22 as that plank is moved past them. Transducers suitable for use in this application are described in U.S. Pat. No. 3,384,767 to J. S. Arnold et al., issued May 21, 1968, hereby incorporated by reference. The transducers 74 and 76 are held against the edges of plank 22 by a constant force from corresponding pneumatic cylinders (not shown).

The piezoelectric transducer 74 is connected to a driving circuit (not shown), such as are well known in the art, to couple an acoustic pulse approximating that produced by the hammer 60 of FIG. 2 into the left edge of the plank 22. The pulse generation circuitry simultaneously activates the start input of the timer 68.

The opposed piezoelectric transducer 76 detects the acoustic pulse as transmitted through the plank 22 and is connected through appropriate amplification and filtering circuitry (not shown) to the stop trigger 58 as shown in FIG. 2 to stop the timer 68.

As the plank 22 progresses along the direction of its grain 20 through the apparatus of FIG. 4, multiple measurements may be made at periodic points along the plank 22 to determine the extent of wetwood conditions throughout the length of the plank 22.

The above description has been that of a preferred embodiment of the present invention. It will occur to those who practice the art that many modifications may be made without departing from the spirit and scope of the invention. For example, a variety of types of transducer assemblies may be used to generate and receive the acoustic pulse provided that the speed of the acoustic pulse may be determined. Further, although the applicant believes that the primary mechanism causing significant variations in the degree to which lumber accommodates rapid drying is bio-deteriorants creating the above-described wetwood, the invention is not limited to detecting bacterial wetwood but addresses the detection of hard to dry lumber in general. In order to apprise the public of the various embodiment that may fall within the scope of the invention, the following claims are made.

We claim:

1. 1 A method of evaluating the proclivity of un-dried wood of a wood type to degrade during drying, the un-dried wood having a grain orientation, comprising the steps of:
    determining a distance between a first and second point in the un-dried wood;
    generating an acoustic pulse at a first time coupled to the un-dried wood at the first point;
    detecting the presence of the acoustic pulse at the second point at a second time;
    employing the value of the distance and the difference between the first and second times to calculate the speed of the acoustic pulse;
    comparing the speed of the acoustic pulse to a predetermined speed value indicating proclivity of the wood type to degrade upon drying; and
    outputting a value indicating the proclivity of the un-dried wood to degrade upon drying.

2. The method as recited in claim 1 wherein the step of comparing the speed of the acoustic pulse characterizes the wood's proclivity to degrade as lesser if the speed is greater than the predetermined speed value.

3. The method as recited in claim 1 wherein the distance is substantially perpendicular to the grain of the wood.

4. The method as recited in claim 1 wherein the acoustic pulse is produced by the impact of a weight of predetermined mass and velocity against the un-dried wood.

5. The method as recited in claim 1 wherein the first time is determined by detecting the acoustic pulse at the first point.

6. The method as recited in claim 1 wherein the un-dried wood has a moisture content above a fiber saturation point.

7. An apparatus for evaluating the proclivity of un-dried wood of a wood type to degrade during drying, the un-dried wood having a grain orientation, comprising:
    an acoustic pulse transmitting means for coupling an acoustic pulse into a first point in the un-dried wood at a first time;
    an acoustic pulse receiving means for detecting the acoustic pulse at a second point in the un-dried wood at a predetermined distance from the first point at a second time;
    a clock means communicating with the acoustic pulse transmitting means and the acoustic pulse receiving means for determining the relative speed of the acoustic pulse;
    a comparator means for comparing the speed of the acoustic pulse with a speed threshold indicating the proclivity of the wood type to degrade upon drying; and
    an output means for outputting a value indicating the proclivity of the un-dried wood to degrade upon drying.

8. The apparatus as recited in claim 7 wherein the acoustic pulse transmitting means and the acoustic pulse receiving means are arranged so that the distance between the first and second point is substantially perpendicular to the grain of the wood.

9. The apparatus as recited in claim 7 wherein the acoustic pulse transmitting means is a hammer of predetermined mass for striking the un-dried wood and having a means for controlling the velocity of its impact with the un-dried wood.

10. The apparatus as recited in claim 7 wherein the acoustic pulse transmitting means includes a second acoustic pulse receiving means for detecting the acoustic pulse at the first point in the un-dried wood at the first time and communicating this time to the clock means.

* * * * *